United States Patent [19]

Garman et al.

[11] Patent Number: 5,441,867
[45] Date of Patent: Aug. 15, 1995

[54] PRE-ACTIVATED PROTEINS FOR LABELLING OLIGONUCLEOTIDE PROBES

[75] Inventors: Andrew J. Garman, Chester; John R. Parker, Cheshire, both of England

[73] Assignee: Zeneca Limited, London, England

[21] Appl. No.: 815,881

[22] Filed: Jan. 7, 1992

Related U.S. Application Data

[63] Continuation of Ser. No. 620,866, Dec. 4, 1990, abandoned.

[30] Foreign Application Priority Data

Dec. 4, 1989 [GB] United Kingdom ............... 8927365

[51] Int. Cl.$^6$ ............... C12N 11/02; G01N 33/535; A61K 39/44; A61K 39/385
[52] U.S. Cl. ........................... 435/6; 435/188; 435/174; 435/964; 436/544; 436/547; 424/179.1; 424/194.1; 530/391.5; 530/391.9; 530/404; 530/405; 530/406; 530/408; 530/409; 530/816
[58] Field of Search ............... 530/591.1, 391.3, 391.5, 530/391.7, 341.9, 404, 405, 406, 408, 409, 410, 816; 435/177, 188, 174, 28, 21, 207, 192, 194, 964, 6, 7.9, 7.92; 436/544, 547; 422/61; 424/178.1, 179.1, 194.1

[56] References Cited

U.S. PATENT DOCUMENTS

| | | | |
|---|---|---|---|
| 4,176,006 | 11/1979 | Cormier et al. | 435/174 |
| 4,232,119 | 11/1980 | Carlsson et al. | 435/7.9 |
| 4,496,658 | 1/1985 | Kondo et al. | 436/510 |
| 4,517,290 | 5/1985 | Iwasa et al. | 435/7.93 |
| 4,529,712 | 7/1985 | Jou et al. | 436/519 |
| 4,810,638 | 3/1989 | Albarella et al. | 435/7 |
| 4,873,187 | 10/1989 | Taub | 435/5 |
| 4,981,979 | 1/1991 | Sivam | 548/545 |
| 4,994,385 | 2/1991 | Bieniarz et al. | 435/177 |
| 5,024,834 | 6/1991 | Houston et al. | 424/85.91 |

FOREIGN PATENT DOCUMENTS

| | | | |
|---|---|---|---|
| 212951 | 3/1987 | European Pat. Off. | C07H 21/00 |
| 0227351 | 7/1987 | European Pat. Off. | G01N 33/68 |
| 2311495 | 8/1987 | European Pat. Off. | C12Q 1/68 |
| 0314127 | 5/1989 | European Pat. Off. | C07D 207/46 |
| 0396116 | 11/1990 | European Pat. Off. | G01N 33/547 |
| 2192889 | 1/1988 | United Kingdom | C07H 19/10 |
| 2199945 | 7/1988 | United Kingdom | C12Q 1/68 |
| 8403520 | 9/1984 | WIPO | C12Q 1/68 |
| 8906701 | 7/1989 | WIPO | C12Q 1/68 |

OTHER PUBLICATIONS

Ji (1983) Methods Enzymol 91: 580–609.
Hasida et al. (1984) J. Appl. Biochem 6: 56–63.
Blair et al (1983) J. Immunol. Method 59:129–143.
Cheng et al (1983) Nucleic acids Res. II (3): 659–669.
Hoffman et al (1988) J. Immunological Methods 112: 113–120.
Yoshitake et al (1982) J. Biochem. 92:1413–1424.
BioRad Catalog (Mar. 1989) pp. 57,166,167.
Stragene Catalog (1989) pp. 64,65.
O'Sullivan et al (1981) Methods Enzymol 73:147–165.
Wang et al (1988) J. Parenteral Science Tech. Suppl. 42 (25): S3–S26.
Chemical Abstracts, vol. 95, 1981, p. 398, Novel Compound for Immunochemical Analysis abstract No. 76514C.
Patent Abstracts of Japan, vol. 5, No. 8 (C–39) (680) 20 Jan. 1981 & JP–A–55 136 261 (Toyo Jozo K.K.) 23 Oct. 1980.
Pierce Chemical Co., Pierce 1989 Handbook & General Catalog (1988).
Pierce Chemical Co., ImmunoPure Activated Phosphatase Instructions, pp. 1–8 (1989).
Pierce Chemical Co., ImmunoTechnology Catalog & Handbook (1990).

*Primary Examiner*—Kay K. A. Kim
*Attorney, Agent, or Firm*—Cushman Darby & Cushman

[57] ABSTRACT

Pre-activated stable protein reagents are provided. The reagents can be made by reaction of the protein and a heterobifunctional linker and have extended stability especially after lyophilisation. The reagents can be used in assay kits to form conjugates with proteins e.g. antibodies or polynucleotides e.g. oligonucleotides probes.

19 Claims, 3 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 22 base pairs
( B ) TYPE: nucleic acid
( C ) STRANDEDNESS: single (D) TOPOLOGY: linear (ii) MOLECULE TYPE: DNA (genomic)

(xi) SEQUENCE DESCRIPTION: SEQ ID NO:1:

GTGGATAGGG TGGATAGGGT GG    22

PRE-ACTIVATED PROTEINS FOR LABELLING OLIGONUCLEOTIDE PROBES

This is a continuation of application Ser. No. 07/620,866, filed on Dec. 4, 1990, which was abandoned upon the filing hereof.

The present invention relates to stable pre-activated protein derivatives and their use in the preparation of protein-polynucleotide and protein-protein conjugates. The conjugates are useful in analytical and diagnostic methods and the protein-polynucleotide conjugates are particularly useful as hybridisation probes, for example in diagnostic methods and in methods of genetic characterisation. The invention also relates to methods for preparing the stable pre-activated protein derivatives and to kits comprising these.

Detection of nucleic acid sequences has hitherto mainly involved the hybridisation of a complementary nucleic acid sequence which has been radiolabelled with, for example 32P or 35S. For reasons of safety and convenience, efforts have been made to replace these labels with non-isotopic labels such as enzymes, fluorophores and chemilumophores.

European patent specification No. 0202758 A discloses oligonucleotide-enzyme conjugates which are useful as hybridization probes to discriminate between nucleotide sequences differing by as little as a single nucleotide. This approach has proved to be most useful and has been widely adopted (for example, J. C. Edman et al., Nucl. Acids Res., 1988, 16, 6235 and J. J. Oprandy et al., J. Clin. Microbiol., 1988, 26, 92). Various methods have since been proposed for achieving covalent linkage between nucleic acid and a protein label or marker moiety. A particularly convenient way of achieving this is by the use of oligonucleotides having a linker moiety which terminates in a thiol function. The thiol function is reacted with an enzyme which has been preactivated to a thiol function thereby achieving indirect covalent linkage of a protein and an oligonucleotide. This approach is illustrated in P. Li et al., Nucl. Acids Res., 1987, 15, 5275 and our above mentioned European patent application.

It will be appreciated that the above method, like all other methods for the covalent linkage of nucleic acid and a protein involve certain reaction steps. These require an understanding of the relevant chemistry in order to prepare conjugates of a reasonable quality on a reproducible basis. There therefore exists the need to provide improved reagents and methods relating to conjugation which can be carried out by a relatively unskilled user and which requires a minimum of instrumentation and specialised techniques.

According to a first aspect of the present invention there is provided a stable protein reagent pre-activated for covalent coupling to a thiol group of a thiolated polynucleotide or to a thiol group of a thiol containing protein.

By the expression "stable" we mean that the reagent of the invention has an acceptable shelf life, for example when included in a kit, of at least one month, conveniently at least three, six or nine months and preferably 12 months. The above periods of time refer to storage at a convenient temperature, for example at room temperature although lower temperature, e.g. below 10 degrees centigrade such as 4-6 degrees centigrade or −15 to −25 degrees centigrade can be used if desired. It will be appreciated that the required stability of the reagent is such that degradation for example due to hydrolysis, polymerisation or other side reactions should not proceed to an extent which prejudices the usefulness of the reagent. In situ preparation of activated proteins for covalent coupling, for example for immediate use was hitherto believed to be required to obviate these problems.

By the expression "pre-activated" we mean that the protein is chemically modified for covalent coupling to a thiol group of a thiolated polynucleotide or to a thiol group of a thiol containing protein. Chemical modification is conveniently effected using a cross-linking agent, preferably a heterobifunctional cross-linking agent having both a group capable of reacting with protein functional groups, for example with protein amino groups, and also having a further group capable of reacting with thiol groups. The latter is conveniently selected from haloacetyl, haloacetamidyl, maleimido, activated disuphide, thiols (under oxidising conditions) and heavy metal derivatives such as mercury derivatives. A preferred group capable of reacting with thiol groups is a maleimido group. Such groups are conveniently joined by an optionally substituted saturated or unsaturated hydrocarbon skeleton containing for example up to 12, up to 10, up to 8, up to 6 or up to 4 carbon atoms and conveniently up to 6 carbon atoms. Examples of optional substitutents include hydroxyl groups. It will be appreciated that the chosen substituents should not interfere with the linking chemistry. Several such reagents have been described in the literature. These include reagents described in the Pierce Catalogue published by the Pierce Chemical Company. Convenient examples include:

reagent        ref $R^1 = H$ (SMCC)    Yoshitake et al, 1979, Eur J. Biochem, 101, 395-399

$R^1 = SO_3Na$    Hashida S. et al, 1984, J. Applied Biochem., 6, 56-63

-continued

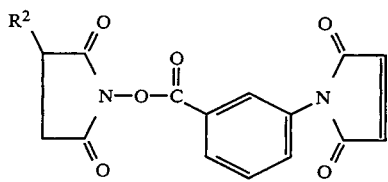

| R² = H (MBS) | Kitagawa T & Aikawa T, 1976 J. Biochem. 79, 233–236 |
| R² = SO₃Na | Catalogue of the Pierce Company |

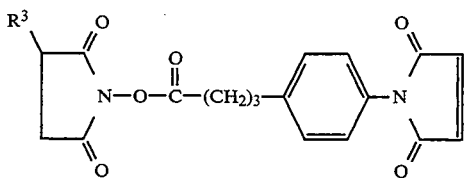

| R³ = H (SMPB) | Martin F J and Papahadjopolous D., 1982, J. Biol. Chem. 257, 286–288 |
| R³ = SO₃Na | Bangs J D et al, 1986, J. Cell. Biol., 103, 255–263 |

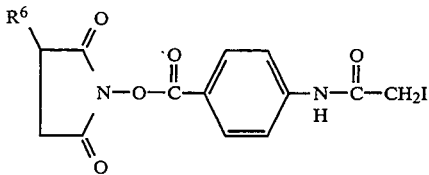

| R⁴ = H (SIAB), SO₃Na | Weltman J K, 1983, Bio Techniques, 1, 148–152 |

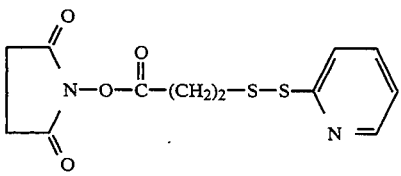

| (SPDP) | Carlson J. et al, 1978, Biochem. J., 173, 723–737 |

A particularly convenient reagent is the succinimidyl 4-(maleimidomethyl) cyclohexane-1-carboxylate (SMCC) linker as described and prepared by Yoshitake et al, European Journal of Biochemistry, (1979), 101, 395–399.

The protein reagent is conveniently an antibody, enzyme or specific binding substance such as avidin, streptavidin or antibody. The protein reagent is conveniently an enzyme. Examples of enzymes include alkaline phosphatase, peroxidases such as horse radish peroxidase (HRP), beta galactosidase, xanthine oxidase, firefly or bacterial luciferase. A preferred enzyme is alkaline phosphatase. The enzyme is, where appropriate, preferably in a heat stable form. Engineered proteins are included.

By "thiolated polynucleotide" we mean a polynucleotide such as an oligonucleotide which has been derivatised to give one or more pendant thiol groups. The polynucleotide can be any nucleic acid such as DNA, RNA, or their analogues; it can be in single or double stranded form and it can be a nuturally occurring material or a synthetic product. In particular, the polynucleotide can be a synthetic single stranded oligonucleotide. Thiol groups can be incorporated into the polynucleotides by chemical or enzymatic routes. For oligonucleotides, chemical methods are convenient. Several methods for the incorporation of thiol groups are known, for example, P. Li et al., Nucl. Acids Res., 1987, 15, 5275 and our European patent application 207758. The thiol group is generally attached to the oligonucleotide via one or more spacer arms which generally comprise a straight hydrocarbon chain of between 2 to 6 carbon atoms joined to the oligonucleotide usually via a moiety such as carbonyl or phosphoryl which is a result of the method used to attach the linker to the said oligonucleotide. We have found that a convenient and advantageous linker is constructed by first synthesising 5'-aminoalkyl derived oligonucleotides such as

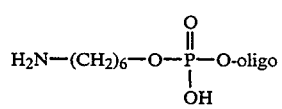

and

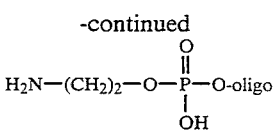

(where 'oligo' means an oligonucleotide) and subsequently reacting with a thiolating reagent such as (especially) 2-iminothiolane and homocysteine thiolactone: 2-iminothiolane (typically used as the hydrochloride-Traut's reagent):

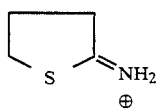

homocysteine thiolactone:

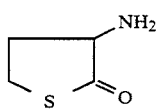

(or its N-acetylated derivative), to give thiolated oligonucleotides such as

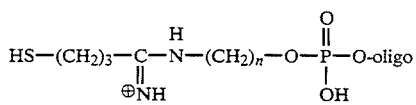

(wherein n is e.g. 6 or 2 and 'oligo' means an oligonucleotide).

By "thiol containing protein" is meant any proteinaceous species which contains one or more native thiol groups, or thiol groups that have been introduced, for example by reduction of native protein disulphide groups or by reaction with thiolating agents such as the 'one step' reagents described above or using 'two step' reagents.

The stable protein reagent is preferably provided in lyophilised form. We have unexpectedly found that proteins that have been derivatised with thiol-reactive moieties such as maleimido or iodoacetamidyl functions, can be lyophilised and that the resulting pre-activated reagents are stable and can be used for the covalent synthesis of nucleic acid conjugates after considerable periods of time.

Therefore according to a further aspect of the present invention we provide a stable lyophilised protein reagent pre-activated for covalent coupling to a thiol group of a thiolated polynucleotide or to a thiol group of a thiol containing protein.

Lyophilisation is generally effected from a solution which is able to maintain the activity of the protein concerned and the reactivity of the thiol reactive functional groups. Such solutions may contain carbohydrates, in particular sugars such as mannitol, lactose or trehalose, or volatile salts, such as ammonium bicarbonate or salts of organic acids or bases. We have achieved particularly good results using lactose in the lyophilisation solution especially at a concentration of about 1%. The solution is desirably buffered at a pH in the range 6 to 8, particularly 7.2 to 7.8 especially about 7.4. In respect of SMCC derivatised alkaline phosphatase, lactose is a preferred sugar and a preferred lyophilisation buffer is 1% lactose, 5 mM NaH$_2$PO$_4$/Na$_2$HPO$_4$, pH 7.4. It is preferred that nucleophilic buffer components are avoided where these are reactive toward the pre-activated protein reagent, especially towards the thiol reactive group. Non-volatile salts may be tolerated but they should preferably be at a low concentration, for example, less than 10 mM. In the case of activated proteins where the thiol-reactive function is labile to hydrolysis, lyophilisation should be carried out soon after the preparation of the derivative. Other components known or found to stabilise the protein may also be conveniently included.

Preferably the cross-linking agent used to chemically modify the protein is present in a controlled quantity, to give a low and controlled degree of substitution. Preferably the degree of substitution should be less than 3 moles per mole of protein, more preferably between 1 and 2, for example 1.4 to 1.6. This low, controlled degree of modification gives an activated protein reagent that is stable and gives conjugate mixtures with a high content of 1:1 conjugates.

The degree of substitution is best controlled by emperical optimisation of the concentration of cross-linking agent but may also be controlled by other factors such as temperature, pH, and length of reaction. Suitable assays for measuring the degree of substitution can be readily devised by the skilled man. For example assays may be devised wherein a sample of the modified protein is reacted with an excess of a thiol compound of known concentration and measuring the amount of thiol compound which is left after the reaction.

A preferred stable protein reagent of the invention comprises alkaline phosphatase derivatised by the SMCC cross-linking agent. This is preferably in lyophilised form, preferably having been lyophilised from 1% lactose, 5 mM NaH$_2$PO$_4$/Na$_2$HPO$_4$, pH 7.4.

The length of the polynucleotide will depend on the purpose for which the polynucleotide signalling conjugate is to be used. Where this is used as a hybridisation probe convenient oligonucleotide lengths are up to 50 such as 1–40, up to 40 such as 20–40, up to 30 such as 10–30, and up to 20 such as 10–20 nucleotides. The nucleic acid is conveniently DNA or RNA or analogues thereof, for example DNA and may be present in single stranded or double stranded form. Conveniently at least the part of the nucleic acid sequence intended for hybridisation will be in single stranded form. Preferably the nucleic acid is all present in single stranded form. Conveniently the polynucleotide sequence, for example a DNA sequence, is synthetically prepared to enable thiol containing groups to be attached. Methods and apparatus for such synthesis will be apparent to the molecular biologist or chemist of ordinary skill using known methods, for example as described in "Oligonucleotide Synthesis, a practical approach" edited by M J Gait, IRL Press, Oxford (1984) and the other references cited above.

Where the stable protein reagent is used in the preparation of protein-protein conjugates a particularly useful further protein is an antibody, or fragment thereof, conveniently for use in immunoassay, in particular in enzyme immunoassay, western blotting, histochemistry and other immunochemical techniques.

A further aspect of the invention provides for a kit to enable the user to prepare conjugates. Such a kit will comprise the stable pre-activated protein reagent and instructions for use, together with optionally a desiccant to prolong storage.

Conveniently the kit will also comprise one or more of the following components:
1. an amount of solid thiolating agent, for example 2-iminothiolane,
2. a pre-packed column for removing excess thiolating reagent from the thiolated product, preferably, this should be a gel filtration column containing, for example Sephadex G25M (Pharmacia),
3. buffer for equilibrating and/or running the column in 2.
4. buffer for reconstituting the thiolating agent.
5. a further column for the purification of the conjugate, conveniently this is a pre-packed gel filtration column containing for example Biogel P100 (Biorad),
6. buffer for equilibrating and/or running the column in 5,
7. stands for mounting the columns,
8. vials for collecting the product and intermediates,
9. an agent for quenching excess thiol reactive groups after conjugation,
10. additives to stabilise the conjugate for prolonged storage,
11. instructions for carrying out the procedure.

It will be appreciated that the stable activated protein reagent may be used to form conjugates with thiol containing or thiolated components other than oligonucleotides and other proteins, for example other nucleic acid species, oligo- or polysaccharides, peptides, haptens and drugs, and that the stable protein reagent and the kit of this invention is not limited by the component that is conjugated to the reagent of this invention.

BRIEF DESCRIPTION OF THE DRAWINGS

The invention is illustrated by the following Examples and Figures. In the Figures

Abbreviations

Figure 1A:
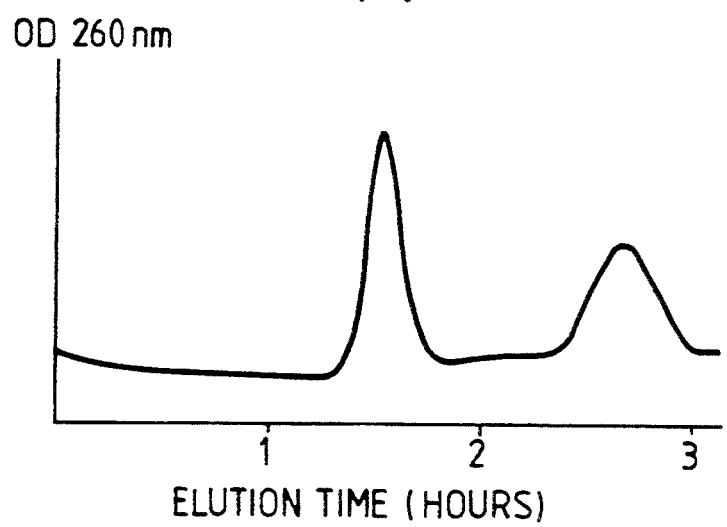
FIG. 1 illustrates Biogel P-100F elution profiles for the purification of FIG. 1(a) the conjugate described in Example 3 and FIG. 1(b) the conjugate described in Example 4.

The following abbreviations apply to the examples:

| | |
|---|---|
| SMCC | succinimidyl 4-(N-maleimidometlyl)cyclohexane-1-carboxylate |
| SIAB | N-succinimidyl(4-iodoacetyl)aminobenzoate |
| Tris | tris(hydroxymethyl)aminomethane |
| BSA | bovine serum albumin (Boehringer molecular biology grade) |
| PBS | 0.13M NaCl, 5.4 mM $Na_2HPO_4$, 1.6 mM $KH_2PO_4$ buffer pH 7.3 |
| SSC | 20x SSC is 3M NaCl, 0.3M trisodium citrate |
| PVP | polyvinylpyrrolidone |
| SDS | sodium dodecyl sulphate |
| DMF | dimethyl formamide |
| HRP | horse radish peroxidase |
| TBS | 1 x TBS is 25 mM Tris, pH 8.1, NaCl 150 mM |
| $PBS^1$ | 6 mM sodium phosphate, pH 7.5, 150 mM NaCl |

EXAMPLE 1

Preparation of lyophilised maleimido alkaline phosphatase

To a solution of alkaline phosphatase (Boehringer, 10 mg/ml, 0.2 ml) was added 0.1M triethanolamine HCl, 1 mM $MgCl_2$, 1 mM $ZnSO_4$, pH 7.4 (0.6 ml), followed by 12 μl of a freshly prepared solution of SMCC (Pierce) in dry DMF (6.7 mg/ml) and the reaction mixture incubated at 25° C. for 30 min. The product was then purified by passage through a NAP 25 desalting column (Pharmacia), primed with BSA and equilibrated in phosphate buffer PBS containing 10 g/l D-mannitol. The product was collected in 1.6 ml and a portion taken for analysis. Protein concentration was assessed by OD at 280 nm (using an extinction coefficient of 0.89 for a 1 mg/ml solution) whilst the maleimido concentration was assessed as follows: 0.15 ml of sample was reacted with 10 μl of 1 mM mercaptoethanol for 30 min. at 37° C., alongside a control with 0.15 ml of buffer alone. The reactions were then diluted with 1.2 ml of PBS, zeroed at 412 nm in a spectrophotometer, and 25 μl of 1 mM 5,5'-dithiobis(2-nitrobenzoic acid) added. Remaining thiol concentrations were thereby measured using an extinction coefficient of 14150, the difference between sample and control enabled the maleimido concentration and hence the degree of substitution to be calculated. This value was found to be between 1.4 and 1.6 moles maleimido per mole of protein. The derivatised enzyme was then aliquoted into 3 nmole portions and lyophilised.

EXAMPLE 2

Preparation of an aminoalkyl oligonucleotide

The following aminoalkyl oligonucleotide (see SEQ. ID NO:1) was synthesised on a 1.0 μmole scale (nominal) on an Applied Biosystems automated DNA synthesiser using protocols recommended by the manufacturer:

AL-GTGGATAGGGTGGATAGGGTGG

AL represents the linker group

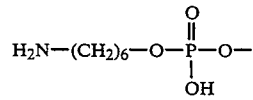

which is derived from the phosphoramidite

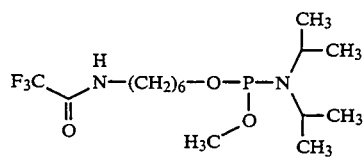

and incorporated during the synthesis as described by the manufacturer. After deprotection and evaporation, the sample was redissolved in 1.0 ml of water.

EXAMPLE 3

Preparation of an oligonucleotide alkaline phosphatase conjugate

Example 1 describes a key component of one of the possible kits of the invention. This example describes the use of this component to make the desired conjugate. Other components are required and some or all of these may be provided as part of the kit.

0.01 ml of the aminoalkyl oligonucleotide was diluted to 0.2 ml with water. To a vial of 2-iminothiolane (4 mg) was added 1.0 ml of 0.2M sodium bicarbonate buffer pH 9.2; 0.3 ml of this solution was immediately added to the oligonucleotide solution. The reaction was incubated at 37° C. for 30 minutes and then applied to a NAP 25 desalting column equilibrated in PBS. After the sample was absorbed onto the column, 2.2 ml of running buffer was added, discarding the eluent. After this portion had been applied, the vial containing the derivatised enzyme (Example 1) was placed under the column and 1.6 ml of buffer applied to the column to elute the thiolated oligonucleotide. The eluted sample was shaken gently to dissolve the enzyme and the reaction allowed to proceed at 4° C. for 16 hours. The sample was then divided into two.

One half was concentrated to ca. 0.3 ml using a microconcentrator (Amicon) and applied to a column (ca. 35 ml) of Biogel P-100F (Biorad) equilibrated and run in 50 mM Tris buffer pH 7.5 at a flow rate of 0.14 ml/min. The eluted peaks were detected by UV absorbance at 260 nm (see FIG. 1a) and UV spectra of the fractions comprising the first peak, containing the conjugate were determined. Fractions in this first peak were pooled. A sample was treated with a 30 fold molar excess of mercaptoethanol for 15 minutes at ambient temperature. For prolonged storage of the conjugate $NaN_3$ and BSA (molecular biology grade) were added to 0.2% and 0.2%, respectively.

The second half was not purified, but treated with mercaptoethanol, BSA and $NaN_3$ as described above.

EXAMPLE 4

Stability of the lyophilised maleimido alkaline phosphatase preparation

Figure 1B:
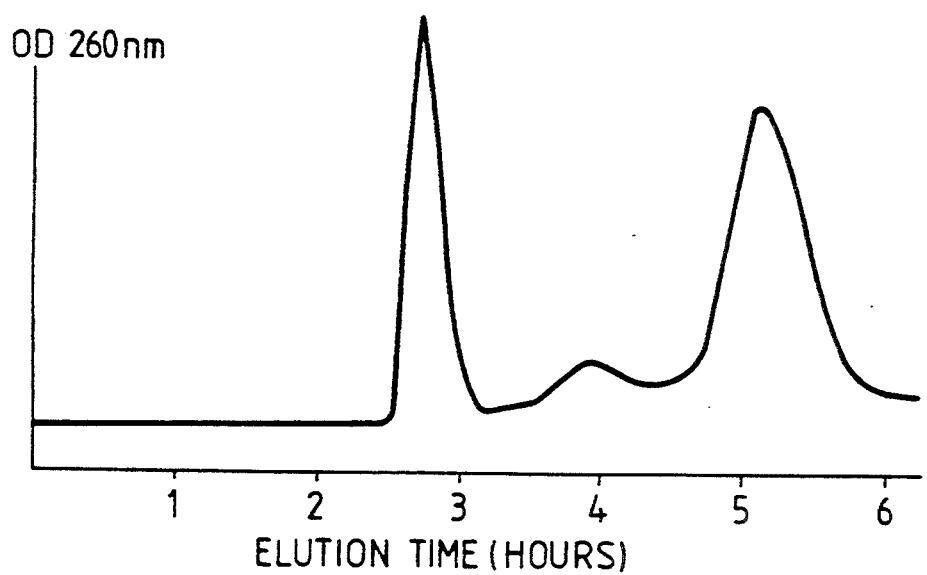
Figure 2A:
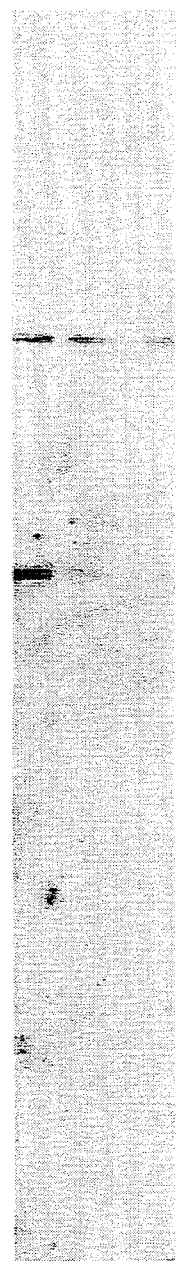
FIG. 2 shows Southern Blots of a Hinf I human DNA digest probed with FIG. 2(a) the purified and FIG. 2(b) the unpurified conjugates of Example 3. The three lanes contain loading of (left to right) 3, 2, and 1 μg of DNA.
Figure 2B:

A sample of lyophilised maleimido alkaline phosphatase that had been stored with desiccant at 4° C. for 3 months was conjugated and purified as described above (but using a ca. 70 ml column). FIG. 1b shown the elution profile obtained. The OD 260/280 ratio was found to be >1.0, which, together with the shape of the elution profile, demonstrates that the stored material had retained its ability to conjugate.

EXAMPLE 5

Use of the conjugates in Southern blotting

Nylon filter Southern blots of human DNA digested with Hinf I were prepared essentially as described by A J Jeffreys et al., Nature, 1985, 314, 67. The filters were then pre-wetted in SSC and then rolled and placed in plastic boxes. These containers were incubated in 5×SSC, 1% SDS, 0.1% BSA, 0.1% Ficol 400 (Pharmacia), 0.1% PVP 44000 (BDH) for 2 hours at 50° C. in an orbital incubator. The conjugate was then added to the container to a concentration of 1.0 nM and allowed to incubate with rotation for 20 minutes at 50° C. The filters were then transferred to a box containing 0.5% SDS in 1×SSC, and washed in the incubator for 5 minutes at 50° C. This wash step was repeated twice, followed by two further wash steps in 0.25×SSC, 0.5% SDS. The filters were then given a final wash in 1×SSC alone, this latter wash was carried out at room temperature. The filters were then sprayed with the chemiluminescent alkaline phosphatase substrate, Lumi-phos (Lumigen Inc.), placed between transparent film in a cassette and exposed to Agfa Curix film for 1.7 hours.

EXAMPLE 6

Preparation of SIAB derivatised freeze-dried alkaline phosphatase

To a solution of alkaline phosphatase (Boehringer, 10 mg/ml, 0.1 ml) was added 0.1M triethanolamine/HCl, 1 mM $MgCl_2$, 1 mM $ZnSO_4$, pH 7.4 (0.3 ml), followed by 7 µl of a freshly prepared solution of SIAB (Pierce) in dry DMG concentration 8.3 mg/ml. The reaction mixture was then incubated at at 25° C. for 30 mins and the product was purified by passage through a NAP 25 desalting column, primed with BSA and equilibrated in PBS. The product was collected in 1.6 ml and split into 2 equal samples (0.8 ml) containing approximately 3 nmoles of derivatised enzyme. The samples were taken frozen at −70° C. and then freeze-dried overnight. Following freeze-drying the vials containing the samples were capped and stored at 4° C. for 1 week prior to conjugation as described in Example 7 below.

EXAMPLE 7

Thiolation of a 5' amino derivatised oligonucleotide with iminothiolane and subsequent conjugation with SIAB derivatised freeze-dried alkaline phosphatase.

An aqueous solution (0.1 ml) of the amino derivatised oligonucleotide (a tenth of a nominal 0.2 micromole synthesis) was added to a vial containing freeze-dried 2-iminsthialane (0.6 mg) and 20 µl of reaction buffer 1M sodium bicarbonate buffer pH 9.2. The content of the vial were mixed to ensure all the 2-iminothiolane reagent dissolved and then incubated at 37° C. for 30 mins. The product was then isolated by passage through a NAP 5 desalting column equilibrated in PBS, collecting the product in 0.6 ml. This was then immediately added to a vial of SIAB derivatised freeze-dried alkaline phosphatase prepared in Example 6 above. After brief mixing the conjugation reaction was allowed to stand overnight at 4° C.

The reaction mixture was then applied to a column (ca 10 ml) of Biogel P-100C (Biorad) equilibrated and run in 50 mM Tris buffer pH 7.5, 0.1% BSA and 0.2% sodium azide. The purified conjugate was recovered in a volume of 1.1 µl and used to probe slot blots in Example 10 below.

EXAMPLE 8

Preparation of maleimido derivatised freeze-dried horse radish peroxidase

A sample of 4.1 mg of HRP (Biozyme) was weighed out and dissolved in 0.1M triethanolamine HCl, 1 mM $Mgcl_2$, 1 mM $ZnSO_4$, pH 7.4 (0.8). To this was added 100 µl of a freshly prepared solution of SMCC in dry DMF (15 mg/ml) and the reaction mixture incubated at 25° C. for 40 mins. The product was then purified by passage through a NAP 25 desalting column primed with BSA and equilibrated in 5 mM phosphate, 1% lactose buffer pH 7.4. The product was collected in 1.6 mls and a sample taken for analysis. The degree of modification was found to be 1.80 moles maleimido per mole of protein.

The remaining sample was diluted to 2.32 ml and dispersed into 200 μl fractions (6 nmoles/vial). These were frozen at −70° C. and then freeze-dried overnight. Following freeze-drying the vials were capped and stored at 37° C. for 1 month prior to conjugation as described in Example 9.

EXAMPLE 9

Conjugation of Donkey anti-sheep antibody with freeze dried maleimido HRP 0.8 ml of Donkey anti-sheep IgG antibody (Scottish Antibody Production Unit, partially purified by ammonia sulphate precipitation) at 1 mg/ml was added to 26 μl of 2-iminothiolane (2 mg/ml in 6 mm sodium phosphate pH 7.5, 150 mm sodium chloride, PBS), 100 μl of 1.0M sodium carbonate buffer pH 9.0 and 74 μl of PBS in a microtest tube. The tube was incubated at 37° C. for 30 minutes and unreacted iminothiolane removed by desalting on a NAP Tri 25 column according to the following procedure. The column was preblocked by the addition of 100 μl of PBS 1% BSA which was then washed through with 15 mls of PBS. The contents of the microtest tube was added to the column and the eluate allowed to run to waste. 1.7 ml of PBS was added to the column and the eluate allowed to run to waste. 1.6 ml of PBS was then added to the column and the eluate collected into a vial containing 6 nmole of freeze-dried maleimido HRP (which had been stored for 1 month at 37° C.). The vial was incubated at +4° C. for 16 hours. The conjugate was then ready for use.

EXAMPLE 10

Preparation of MS1 slot blots (DNA)

Slot blots were mad with MS1 DNA bound to Hybond-N membrane. Dilutions of MS1 were made to the following concentrations (pg/μl): 30, 15, 6, 3, 0.6, 0.2.

Denaturation buffer was prepared as follows: to 14.8 ml of water was added 1.7 ml 1M Tris-HCl, pH 7.5, 3 ml 2M NaOH, and 10 ml of 20×SSC.

5 μl DNA solution was added to 295 μl denaturation buffer and the sample was incubated in a boiling water bath for 10 minutes, transferred to an ice bath and neutralised with 100 μl 1M Tris-HCl pH 7.5. Slot blots were prepared using Hybond-N nylon membrane (pre-soaked in 1×SSC), washing the slots first with 0.4 ml 1×SSC, applying the denatured sample (0.4 ml) and washing the slots with a further 0.4 ml of 1×SSC.

The membrane was air-dried on filter paper for 20 minutes, wrapped in Saran-wrap, UV-irradiated for 4 minutes then air-dried completely.

EXAMPLE 11

Preparation of Sheep IgG dot blots

An affinity purified antibody-raised in sheep at a concentration of 0.9 mg/ml was diluted 1/18 in PBS phosphate, 7.5, 150 mM sodium chloride to give a concentration of 50 ng/ul. Serial dilutions (in PBS) were made to give concentrations of 10, 5, 1, 0.5, 0.1 0.05, 0.01, ng/ul. 1 ul aliquots of each solution was spotted onto a strip of Hybond C extra (Amersham) which was then allowed to dry for 30 minutes.

The following format was used:

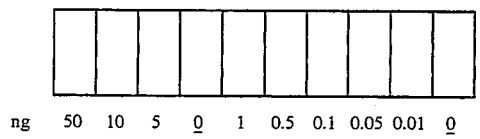

ng  50  10  5  0  1  0.5  0.1  0.05  0.01  0

EXAMPLE 12

Hybridisation of conjugate to slot blots

Slot blots were placed in a sandwich box and incubated in hybridisation solution for 2 hours at 50° C. in a shaking water bath. The hybridisation solution was then replaced with 50 ml of fresh hybridisation solution and 50 ul of DNA probe (Example 7) was added. The filters were incubated in the solution to 20 mins at 50° C. in a shaking water bath. After hybridisation filters were washed twice in wash solution (1×SSC, 0.5% SDS) for 5 mins at 50° C., then twice in wash solution (0.25×SSC, 0.5%) SDS for 5 mins at 50° C. and finally once in 1×SSC for 5 mins at room temperature.

The filters were probed with alkaline phosphatase conjugates and then placed on a plastic tray and sprayed with Lumi-phos and then sealed between acetate sheets in a film cassette. A piece of X-ray film (Fuji) was then placed on the acetate sandwich and the film cassette incubated at 37° C. for 1 hour at 37° C.

Figure 3:
FIG. 3 shows the bands obtained by probing MSI DNA samples on slot blots with the oligonucleotide conjugate MSI mini satellite probe prepared in example 7. The target DNA loading was 150, 75, 30, 15, 3 and 1.5 pg in columns 1, 2, 3, 4, 5 and 6 respectively.

The film was then developed and signal development determined (see FIG. 3).

EXAMPLE 13

Detection of Sheep IgG using Donkey anti-sheep HRP conjugate

Figure 4:
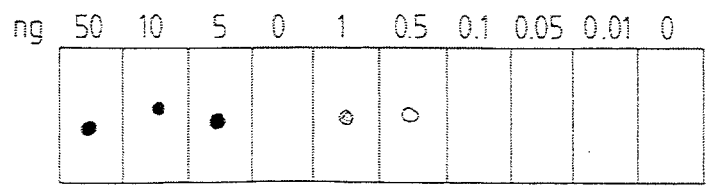
FIG. 4 shows the data obtained by incubating the donkey anti-sheep antibody conjugate prepared in example 9 with the Sheep IgG dot blot prepared in example 11. The target IgG loading was 50, 10, 5, 0, 1, 0.5, 0.1, 0.05, 0.01, and 0 ng as shown.

A sheep IgG dot blot was pre-blocked for 30 mins at room temperature in blocking buffer—0.5% casein, 1×TBS, 0.1% Tween 20 The blot was transferred to blocking solution containing a 1/500 dilution of Donkey anti-Sheep HRP conjugate prepared in example 9. The blot was incubated in this solution for 2 hours at room temperature. The blot was then washed twice in 1×TBS, 0.05% Tween 20 for 15 mins at room temperature, and once in 1×TBS for 5 mins at room temperature. The blot was incubated in substrate buffer (1.5 μl 30% hydrogen peroxide, 4 mg 3,3'-diaminobenzidine tetrahydrochloride in 5 mls 0.1M Tris pH 7.5) for 10 mins, washed in water and allowed to dry. The result is shown in FIG. 4.

---

We claim:

1. An antibody or an enzyme reagent, pre-activated for covalent coupling to a thiol group of a thiolated polynucleotide or to a thiol group of a thiol containing protein, said reagent being lyophilized from a buffered carbohydrate solution having a pH of from 6 to 8 which buffered solution has concentration of non-volatile salts of not more than 10 mM, so as to provided said reagent in dry solid form and being stable for at least 3 months against hydrolysis, polymerization and loss of label activity and of capacity to form conjugate by said covalent coupling.

2. A reagent as claimed in claim 1 pre-activated by reacting said antibody or enzyme to a first reactive group of a heterobifunctional cross-linking agent having first and second reactive groups, which first reactive group is capable of reacting with protein functional groups, the second reactive group of the cross-linking agent being capable of reacting with thiol groups.

3. A reagent as claimed in claim 2 wherein the first reactive group is reactive towards protein amino groups.

4. A reagent as claimed in claim 3 wherein the first reactive group is a succinimido-N-oxy ester group.

5. A reagent as claimed in claim 2 wherein the second reactive group is a maleimido, haloacetyl or haloacetamidyl or an activated disulphide or thiol group.

6. A reagent as claimed in claim 1 wherein the enzyme is alkaline phosphatase or horseradish peroxidase.

7. A reagent as claimed in claim 1 wherein said carbohydrate is lactose.

8. A kit to enable the use of prepared conjugates comprising a pre-activated antibody or an enzyme reagent, pre-activated for covalent coupling to a thiol group of a thiolated polynucleotide or to a thiol group of a thiol containing protein and instructions for use, said reagent being lyophilized from a buffered carbohydrate solution having a pH of from 6 to 8 which buffered solution has a concentration of non-volatile salts of not more than 10 mM, so as to provide said reagent in dry solid form and being stable for at least 3 months against hydrolysis, polymerisation and loss of label activity and of capacity to form conjugate by said covalent coupling.

9. A kit as claimed in claim 8 also comprising one or more of the following components
 a) solid thiolating agent;
 b) a pre-packed column for removing excess thiolating reagent from the thiolated product;
 c) buffer for equilibrating and/or running the column in 2;
 d) buffer for reconstituting the thiolating agent;
 e) a further column for the purification of conjugate;
 f) buffer for equilibrating and/or running the column in 5;
 g) stands for mounting the columns;
 h) vials for collecting the product and intermediates;
 i) an agent for quenching excess thiol reactive groups after conjugation; and
 j) additives to stabilise the conjugate for prolonged storage.

10. A method of making a conjugate which comprises reacting an antibody or an enzyme reagent, pre-activated for covalent coupling to a thiol group of a thiolated polynucleotide or to a thiol group of a thiol containing protein with a thiolated polynucleotide or a thiol containing protein respectively, said reagent being lyophilized from a buffered carbohydrate solution having a pH of from 6 to 8 which buffered solution has a concentration of non-volatile salts of not more than 10 mM, so as to provide said reagent in dry solid form and being stable for at least 3 months against hydrolysis, polymerisation and loss of label activity and capacity to form conjugate by said covalent coupling, and reconstituting said lyophilized reagent in buffer before use.

11. A kit as claimed in claim 9 wherein the thiolating agent is 2-iminothiolane.

12. A kit as claimed in claim 8 comprising also solid thiolating agent.

13. A reagent according to claim 2 in which said antibody or enzyme carries 1 to 3 residues of cross linking agent per molecule of said antibody or enzyme.

14. A kit according to claim 8 in which the reagent is stored in the presence of a desiccant.

15. A reagent pre-activated for covalent coupling to a thiol group of a thiolated polynucleotide or to a thiol group of a thiol containing protein, said reagent comprising a derivatized enzyme selected from the group consisting of alkaline phosphatase and horse radish peroxidase, said derivatization being by a reaction to give 1–3 substituents per enzyme molecule with a heterobifunctional cross-linking agent selected from the group consisting of:

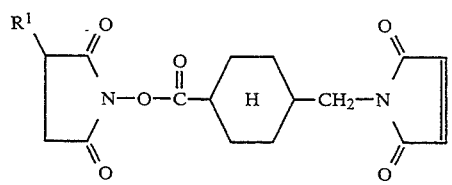

(SMCC) where R1 is H or SO3Na;

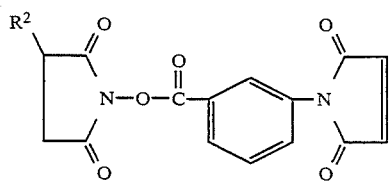

(MBS) where R2 is H or SO3Na;

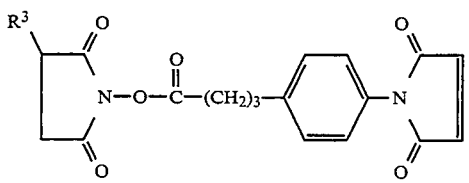

(SMPB) where $R^3$ is H or $SO_3Na$;

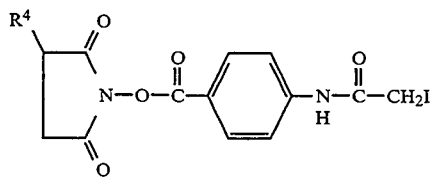

(SIAB) where $R^4$ is H or $SO_3Na$; and

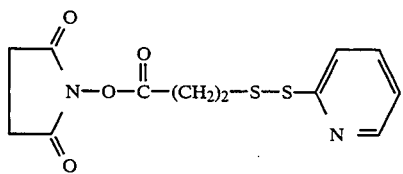

(SPDP)

and said reagent being in dry solid lyophilised form from a buffered carbohydrate solution having a pH of from 6 to 8 which buffered solution has a concentration of non-volatile salts of not more than 10 mM, and being stable for at least 3 months against hydrolysis, polymerisation and loss of label activity and of capacity to form conjugate by said covalent coupling.

16. A storage stable freeze dried reagent pre-activated for covalent coupling to a thiol group of a thiolated polynucleotide or to a thiol group of thiol containing protein, said reagent comprising:
alkaline phosphatase derivatised by 1–3 molecules per phosphatase molecule of the heterobifunctional cross linking agent:

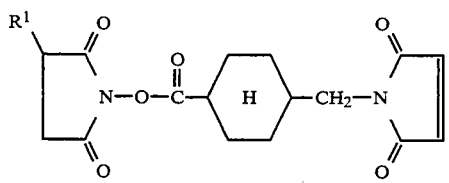

wherein said reagent has been lyophilized from a phosphate buffered solution containing lactose and having a pH of from pH 7.2 to pH 7.8 which buffered solution has a concentration of non-volatile salts of not more than 10 mM, and being stable for at least 3 months against hydrolysis, polymerization and loss of label activity and of capacity to form conjugate by said covalent coupling.

17. A storage stable freeze dried reagent pre-activated for covalent coupling to a thiol group of a thiolated polynucleotide or to a thiol group of a thiol containing protein, said reagent comprising:
alkaline phosphatase derivatised by 1–3 molecules per phosphatase molecule of the heterobifunctional cross linking agent:

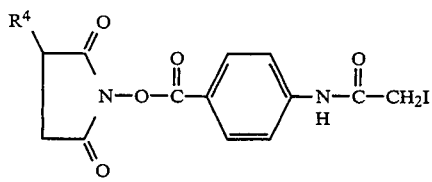

wherein said reagent has been lyophilized from a phosphate buffered solution containing lactose and having a pH of from pH 7.2 to pH 7.8 which buffered solution has a concentration of non-volatile salts of not more than 10 mM, and being stable for at least 3 months against hydrolysis, polymerization and loss of label activity and of capacity to form conjugate by said covalent coupling.

18. A storage stable freeze dried reagent pre-activated for covalent coupling to a thiol group of a thiolated polynucleotide or to a thiol group of a thiol containing protein, said reagent comprising:
horseradish peroxidase derivatised by 1–3 molecules per peroxidase molecule of the heterobifunctional cross linking agent:

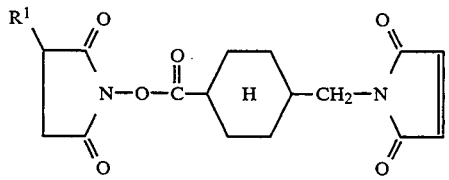

wherein said reagent has been lyophilized from a phosphate buffered solution containing lactose and having a pH of from pH 7.2 to pH 7.8 which buffered solution has a concentration of non-volatile salts of not more than 10 mM, and being stable for at least 3 months against hydrolysis, polymerization and loss of label activity and of capacity to form conjugate by said covalent coupling.

19. In a process for making a conjugate of an enzyme and a polynucleotide or protein by the steps of
(a) derivatising the polynucleotide or protein to apply to it one or more pendant thiol groups;
(b) derivatising the enzyme to apply to it one or more thiol-reactive groups; and
(c) reacting the derivatised polynucleotide or protein with the derivatised enzyme;
the improvement which comprises lyophilizing the derivatised enzyme in a buffered carbohydrate solution having a pH of from 6 to 8 which buffered solution has a concentration of non-volatile salts of not more than 10 mM so as to give a reagent stable for at least 3 months, storing it until required and reconstituting said reagent in buffer before use, whereby to decrease by one the number of chemical reaction stages at the time of making said conjugate.

* * * * *